United States Patent [19]

Eldin et al.

[11] 4,396,782

[45] Aug. 2, 1983

[54] PROCESS FOR PRODUCING UNSATURATED ETHERS

[75] Inventors: Sameer H. Eldin, Birsfelden; Milos Rusek, Binningen, both of Switzerland

[73] Assignee: Ciba-Geigy Corporation, Ardsley, N.Y.

[21] Appl. No.: 337,898

[22] Filed: Jan. 7, 1982

[30] Foreign Application Priority Data

Jan. 15, 1981 [CH] Switzerland ............................ 244/81

[51] Int. Cl.$^3$ .............................................. C07C 41/28
[52] U.S. Cl. .................................... 518/686; 568/691; 568/685; 568/669; 568/579
[58] Field of Search ............... 568/691, 685, 686, 669, 568/579

[56] References Cited

U.S. PATENT DOCUMENTS

| | | | |
|---|---|---|---|
| 3,218,359 | 11/1965 | Aguadisch | 568/691 |
| 3,546,300 | 12/1970 | Williamson | 568/691 |
| 4,014,941 | 3/1977 | Tanaka et al. | 568/691 |

FOREIGN PATENT DOCUMENTS

| | | | |
|---|---|---|---|
| 49-45382 | 12/1974 | Japan | 568/691 |
| 681059 | 10/1952 | United Kingdom . | |

OTHER PUBLICATIONS

W. J. Croxall et al., J. Amer. Chem. Soc. 70, 2805 (1948).

*Primary Examiner*—Howard T. Mars
*Attorney, Agent, or Firm*—Luther A. R. Hall

[57] ABSTRACT

A process for producing $\alpha,\beta$-unsaturated alkenyl ethers by cleavage of acetals in the gas phase and in the presence of a catalyst, the catalyst used being calcium oxide, the acetal cleavage being performed in the temperature range of 200° to 300° C. and the process being carried out preferably in a simple distilling apparatus.

6 Claims, No Drawings

PROCESS FOR PRODUCING UNSATURATED ETHERS

The invention relates to a process for producing unsaturated alkenyl ethers by cleavage of acetals in the gas phase and in the presence of calcium oxide as the catalyst.

It is known from the G.B. Patent Specification No. 681,059 that acetals can be cleaved in the gas phase, in the presence of barium oxide as catalyst, to give alkenylalkyl ethers and alkanols. In this process, it is necessary on the one hand to apply the barium oxide to silica gel as the carrier substance, and on the other hand to maintain the catalyst in suspension during the reaction in which the acetal is cleaved. In order that the catalyst can be kept in suspension, it has to be present in a very finely dispersed form.

It has now been found that the cleavage of acetals in the gas phase can surprisingly be formed technically more simply by using calcium oxide as catalyst in place of the barium oxide on the carrier substance. It is not necessary in the process according to the invention to firstly apply the catalyst to a carrier material; so that consequently this procedure of preparing the catalyst is avoided. Furthermore, the process of the invention eliminates the necessity stated in the G.B. Patent Specification mentioned above of having to retain the catalyst particles in suspension during the cleavage of the acetal. The process according to the invention can by comparison be carried out in a simple distilling apparatus.

The subject matter of the present invention is thus a process for producing an $\alpha,\beta$-unsaturated alkenyl ether of the formula I

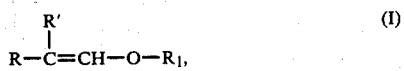

wherein R is a hydrogen atom, methyl or ethyl, and R' is a hydrogen atom or methyl, and $R_1$ is the radical of a monovalent aliphatic or cycloaliphatic alcohol that is unsubstituted or substituted by halogen atoms, by cleavage of an acetal in the gas phase and in the presence of a catalyst, which process comprises cleaving an acetal of the formula II

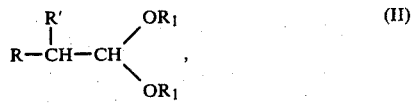

wherein each $R_1$ independently of the other has the meaning defined under the formula I, in the temperature range of 200° to 350° C. in the presence of calcium oxide as catalyst.

Acetals of the formula II preferably used in the process according to the invention are those in which R is -H, methyl or ethyl, especially however H, R' is -H, and each $R_1$ independently of the other is alkyl having 1 to 5 C atoms, which is unsubstituted or substituted by halogen atoms, and in particular they are each alkyl having 2 to 4 C atoms, which is unsubstituted or substituted by chlorine atoms.

The acetal of the formula II used in a preferred embodiment of the present invention is acetaldehyde-bis-(2-chloroethylacetal).

The acetals of the formula II which are used in the process according to the invention are known, and they can be produced for example from the corresponding aldehydes, such as acetaldehyde, propionaldehyde, isobutyraldehyde or butyraldehyde, and from aliphatic or cycloaliphatic alcohols in the presence of small amounts of anhydrous mineral acid or toluenesulfonic acid.

Suitable aliphatic and cycloaliphatic alcohols which may be mentioned are: methanol, ethanol, 2-chloroethanol, isobutanol, allyl alcohol, crotyl alcohol, octyl alcohol, cyclopentanol, cyclohexanol and 4-methylcyclohexanol. The acetal preferably used, namely acetaldehyde-bis-(2-chloroethylacetal), can also be produced from vinyl acetate and ethylenechlorohydrin using the process disclosed by W. J. Croxall et al. in the "Journal of the American Chemical Society", 70, 2805 (1948).

The calcium oxide catalyst to be used according to the invention can be employed either in the pure form or in the commercial form. A carrier material for the calcium oxide is not required. The size of the catalyst particles is not critical, and depends on the particular type of apparatus and mode of carrying out the process. When, for example, the process according to the invention is performed in a simple distilling apparatus, the catalyst is advantageously used, as particles the size of peas, in a packed column. For this purpose is used 10 to 50 percent by weight of CaO particles, preferably 25–30 percent by weight, relative to the total amount of acetal.

The reaction temperature, which in general is between 180° and 350° C., preferably 200°–260° C., and which is governed by the boiling point of the employed acetal, is preferably somewhat above the boiling point of the acetal used, but has to be below the decomposition temperature of the unsaturated ether being formed during the catalytic cleavage operation.

The process according to the invention is performed preferably under normal pressure, the space velocity of the acetal vapours (volume of acetal vapours to volume of catalyst per hour (h) being so adjusted that it is within the range of 36 to 360 $h^{-1}$, preferably 70 to 140 $h^{-1}$. The acetal volume per second is obtained from the reacted amount of acetal and the duration of the performed reaction.

The process according to the invention is advantageously carried out in the presence of an inert gas as carrier gas. The gas particularly suitable for this purpose is nitrogen. The gas flow of acetal vapours can moreover be regulated better with a carrier gas. A carrier gas which is introduced into the acetal liquid contained in the reaction flask serves also as a stirring agent and temperature-regulating agent. When for example the catalytic cleavage of the corresponding acetal is performed in an $N_2$ atmosphere, the flow of nitrogen is preferably so adjusted that the space velocity of the nitrogen is 120 to 900 $h^{-1}$, especially 360 to 480 $h^{-1}$. The volume of $N_2$ per minute can be measured with a rotameter, for example with the "Brooks" small-flowmeter.

The reaction products formed on the catalytic decomposition of the acetal, namely the unsaturated ether and the corresponding alcohol, are condensed by cooling. The unsaturated ether can be readily obtained from the condensed reaction mixture by means of fractional distillation.

The unsaturated ethers obtained by the process according to the invention can be processed, in a known manner, into macromolecular substances by homo- or copolymerisation. The unsaturated ethers obtainable according to the invention are suitable also as starting compounds in the synthesis of other compounds, for example for producing halogen compounds which are obtained by an addition reaction of chlorine or bromine with the reactive double bond.

EXAMPLES 1-4

10 g of acetaldehyde-bis-2-chloroethylacetal are in each case distilled, in the apparatus described below, through a 30 mm deep layer consisting of the respective catalyst. The acetal is then introduced into the Herz flask, and is distilled under a gentle stream of $N_2$ (30–40 cm$^3$/min) under normal pressure. Refluxing occurs at about 190°–200° C. bath temperature. The cleavage products which are formed in the catalyst layer, namely chloroethylvinyl ether and/or chloroethanol, are further transported by the stream of nitrogen and they condense in the sausage flask or at the latest in the condenser. In the further course of the reaction, the bath temperature is raised towards 250° C. in order to ensure an approximately constant rate of distillation. The results are given in Table 1.

EXAMPLE 5

10 g of acetaldehyde-bis-2-chloroethylacetal are distilled as in the above Examples but without the use of a stream of $N_2$ gas. The reaction flask contains two boiling stones in order to avoid any delays in boiling. The result is shown in Table 1. The apparatus used is described below.

The apparatus consists of a 50 ml Herz flask having a gas-inlet at the side, a straight fractionating column, a curved connecting piece and a sausage flask with attached condenser. The sausage flask and condenser are directed upwards so that the occurring condensate can collect in the curved part of the sausage flask. It is possible with this arrangement to easily take, during distillation, samples for the gas-chromatographical analysis. There is introduced in the side inlet of the Herz flask a capillary tube connected to a nitrogen source.

The catalyst is contained, as an approximately 30 mm deep layer, in the straight fractionating column which has a tube inside diameter of 14.5 mm. The column is suitably narrowed in the lower part in order to prevent the catalyst particles from slipping down.

TABLE 1

| | | Cleavage of acetaldehyde-bis-2-chloroethylacetal by means of catalysts | | | |
|---|---|---|---|---|---|
| Examples | Catalyst | Reaction duration [hours] | Reaction temperature [°C.] | Yield of 2-chloro-ethylvinyl ether % of theory | Chloroethanol % of theory |
| 1 | BaO—silica gel[1] | 2 | 203–244 | 0 | >90 |
| 2 | BaO[2] | 3 | 182–236 | 0 | >>96 |
| 3 | CaO[3] | 2.5 | 208–252 | 87 | 67.3 |
| 4 | CaO[3] | 2.25 | 206–248 | 73.1 | 51.3 |
| 5 | CaO[3] | 1.7 | 192–236 | 92.5 | 90.0 |

[1] produced according to G.B. Patent Specification No. 681,059
[2] pure, a "Siegfried AG" product, reduced mechanically to the size of peas
[3] commercial grade, mechanically reduced to the size of peas

What is claimed is:

1. A process for producing an $\alpha,\beta$-unsaturated alkenyl ether of the formula I

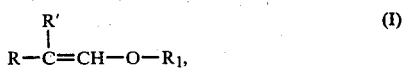

wherein R is a hydrogen atom, methyl or ethyl, and R' is a hydrogen atom or methyl, and $R_1$ is the radical of a monovalent aliphatic alcohol that is substituted by a halogen atom, by cleavage of an acetal in the gas phase and in the presence of a catalyst, which process comprises cleaving an acetal of the formula II

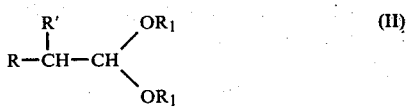

wherein each $R_1$ independently of the other has the meaning defined under the formula I, in the temperature range of 200° to 350° C. in the presence of calcium oxide as catalyst.

2. A process according to claim 1, wherein there is used an acetal of the formula II in which R is -H, methyl or ethyl, and R' is -H, and each $R_1$ independently of the other is alkyl having 1 to 5 C atoms, which is substituted by halogen atom.

3. A process according to claim 1, wherein there is used an acetal of the formula II in which R and R' are each -H, and each $R_1$ independently of the other is alkyl having 2 to 4 C atoms, which is substituted by a chlorine atom.

4. A process according to claim 1, wherein there is used an acetal of the formula II in which R and R' are each -H, and each $R_1$ is 2-chloroethyl.

5. A process according to claim 1, wherein the cleavage of the acetal is performed by means of a simple distillation.

6. A process according to claim 1, wherein the cleavage of the acetal is performed in an $N_2$ atmosphere.

* * * * *